(12) United States Patent
Piper

(10) Patent No.: US 6,390,090 B1
(45) Date of Patent: May 21, 2002

(54) INHALATION THERAPY APPARATUS

(76) Inventor: Samuel David Piper, 3929 Arderly Ct., Sacramento, CA (US) 95826

( * ) Notice: Subject to any disclaimer, the term of this patent is extended or adjusted under 35 U.S.C. 154(b) by 0 days.

(21) Appl. No.: 09/429,243

(22) Filed: Oct. 28, 1999

Related U.S. Application Data

(60) Provisional application No. 60/114,406, filed on Dec. 31, 1998.

(51) Int. Cl.[7] .............................................. A61M 16/00
(52) U.S. Cl. ............................. 128/203.28; 128/200.14; 128/200.18; 128/203.12
(58) Field of Search ....................... 128/200.14, 200.18, 128/200.22, 205.13, 203.28, 204.28, 203.12

(56) References Cited

U.S. PATENT DOCUMENTS

| | | | |
|---|---|---|---|
| 3,967,619 A | 7/1976 | Story et al. | 128/145.8 |
| 4,088,131 A | 5/1978 | Elam et al. | 128/145.7 |
| 4,163,450 A | 8/1979 | Kirk et al. | 128/145.8 |
| 4,173,977 A | 11/1979 | Burns | |
| 4,396,015 A | 8/1983 | Johnson | 128/200.14 |
| 4,484,577 A | 11/1984 | Sackner et al. | 128/203.28 |
| 4,676,239 A | 6/1987 | Humphrey | 128/205.17 |
| 4,823,784 A | 4/1989 | Bordoni et al. | 128/200.14 |
| 5,020,530 A * | 6/1991 | Miller | 128/203.28 |
| 5,099,833 A | 3/1992 | Michaels | 128/200.14 |
| 5,178,138 A * | 1/1993 | Walstrom et al. | 128/200.23 |
| 5,287,847 A | 2/1994 | Piper et al. | 128/200.21 |
| 5,287,849 A | 2/1994 | Piper et al. | 128/203.12 |
| 5,479,920 A | 1/1996 | Piper et al. | 128/204.23 |
| 5,533,502 A | 7/1996 | Piper | 128/203.21 |
| 5,586,551 A * | 12/1996 | Hilliard | 128/203.29 |
| 5,613,489 A * | 3/1997 | Miller et al. | 128/203.28 |
| 5,701,886 A * | 12/1997 | Ryatt | 128/203.12 |
| 5,752,502 A | 5/1998 | King | |
| 5,842,467 A * | 12/1998 | Greco | 128/200.23 |
| 5,848,587 A * | 12/1998 | King | 128/200.18 |

* cited by examiner

*Primary Examiner*—John G. Weiss
*Assistant Examiner*—Mital Patel
(74) *Attorney, Agent, or Firm*—Townsend and Townsend and Crew, LLP

(57) ABSTRACT

An inhalation therapy device includes a collapsible aerosol storage bag (7) having an opening which connects to the end of a dual port member, one port (8) of which is in fluid communication with a nebulizer. During patient exhalation the aerosol storage bag becomes partially inflated with exhaled gas during the first part of exhalation. The laminar coherent aerosol jet exits the dual port member and remains coherent until reaching the end of the aerosol storage bag, at which time it diverges and expels all exhaled gas from the aerosol storage bag, thus filling the aerosol storage bag with aerosol. All escaping gas exits the aerosol storage bag via the remaining port (9) of the dual port member, where it escapes into the ambient environment through the ambient port. The remaining dual port of the dual port member, in addition to providing means for escaping gas from the aerosol storage bag, is also in fluid communication with the ambient port and the mouthpiece (1). Upon inhalation, the patient inhales the aerosol within the aerosol storage bag, the aerosol produced by the nebulizer during inhalation, and ambient air through the ambient port. The cycle is than repeated indefinitely.

9 Claims, 3 Drawing Sheets

INHALATION THERAPY APPARATUS

CROSS-REFERENCE TO RELATED APPLICATION

This claims the benefit of U.S. Provisional Patent Application No. 60/114,406 filed Dec. 31, 1998.

BACKGROUND OF THE INVENTION

1. Field of the Invention

This invention pertains generally to inhalation therapy devices, and more particularly to a inhalation therapy device which may be used in conjunction with a nebulizer to store medicinal aerosol during patient exhalation, to be delivered the subsequent patient inhalation.

2. Description of the Background Art

Inhalation delivery systems of various types have been widely used for inhalation delivery of aerosols containing medication or other constituents to the conductive airways of the lung and the gas exchange regions of the deep lung. Aerosols are relatively stable suspension of finely divided droplets or solid particles in a gaseous medium, usually in air. When inhaled, aerosol particles may be deposited by contact upon the various surfaces of the respiratory tract leading to potential injury, desirable therapeutic action, or planned diagnostic behavior depending on the particular properties of the particles. Inhalable aerosols are those consisting of particles between 1 and 5 micrometers in aerodynamic equivalent diameter.

Because of the high permeability of the lung and the copious blood flow, medications depositing in the lung can readily enter the blood for action throughout the body, while other medications can directly influence the airway epithelium and effect responses via various airway receptors. Properly generated and formulated aerosols can therefore be helpful in medical treatment. As tracers of airflow or indicators of lung responses, other types of aerosol particles deposited in the lung can also be a valuable diagnostic tool.

A nebulizer produces aerosol of fine particles by breaking a fluid into fine droplets and dispersing them into a flowing stream of gas. The droplet size from a medical nebulizer is considerably smaller than a conventional spray atomizer. Medical nebulizers are designed to convert water or aqueous solutions or colloidal suspensions to aerosols of fine, inhalable droplets that can enter the lungs of a patient during inhalation and deposit on the surface of the respiratory airways.

Pneumatic (compressed gas) medical nebulizers heretofore developed typically provide approximately 15 to 30 microliters of aerosol per liter of gas in finely divided droplets with volume or mass median diameters in the respirable range of 2 to 4 micrometers. Nebulizer gas flow rates typically vary between 6 and 8 L/min.

The inhalation therapy device most often used in conjunction with the nebulizer typically consists of a tee, mouthpiece, and storage tube. The tee consists of 3 branches with corresponding ports for connection of the nebulizer, mouthpiece, and storage tubing. The mouthpiece provides the means for connection to the patient. The storage tube is typically 60 ml in volume and is intended to store some of the aerosol produced by the nebulizer during exhalation. The nebulizer is connected to a compressed gas source and aerosol is caused to flow into the tee and, during inhalation, to the patient. During exhalation the volume and flow of the exhaled gas from the patient is far greater than the flow coming from the nebulizer, resulting in almost the majority of aerosolized medication delivered by the nebulizer entering the ambient environment, where it is lost to the patient. More effective means of storing aerosol can not be realized by increasing the volume of the storage tube because it causes the patient to rebreathe an unacceptable amount of exhaled gas.

A widely used device, the Circulaire, works in conjunction with a nebulizer as previously described and attempts to circumvent the problem of rebreathed gas by storing aerosol in a collapsible aerosol storage bag and is similar to the device described and illustrated in U.S. Pat. No. 5,020,530. The Circulaire prevents exhaled gas from entering the aerosol storage bag through means of a check valve which allows only gas and aerosol to exit the aerosol storage bag. This approach is not very successful because much of the medication stored in the aerosol storage bag is lost as the result of impaction of aerosol particles on the check valve resulting in less medication delivered to the patient than with the previously mentioned tee. The check valve within the Circulaire also has the additional disadvantage of changing the mass median aerodynamic diameter of the aerosol to less than 1 micron, which is below the practical respirable range for aerosol deposition within the human lung.

Therefore, a need exists for a inhalation therapy device which can work in conjunction with a nebulizer to store aerosol produced by the nebulizer during the patients exhalation to be delivered to the patient on the subsequent inhalation. The present invention satisfies that need and has the further advantage of not adversely affecting the mass median aerodynamic diameter of the aerosol delivered to the patient.

SUMMARY OF THE INVENTION

The present invention generally pertains to a inhalation therapy device designed to function with existing nebulizers and provides the means for a more effective and inexpensive aerosol therapy than prior art.

By way of example and not of limitation, the present invention employs a collapsible aerosol storage bag. The aerosol storage bag has one opening which connects to the end of a dual port member. One port is in fluid communication with the connecting port for the nebulizer. The geometry of the port in fluid communication with the connecting port for the nebulizer is such that the flow of gas exiting the dual port member and entering the aerosol storage bag is a coherent laminar jet. A coherent laminar jet has the two primary properties of retaining roughly the same cross sectional area of the port of exit and not mixing with the other gas already in the aerosol storage bag. During patient exhalation the aerosol storage bag becomes partially inflated with exhaled gas during the first part of exhalation. The laminar coherent aerosol jet exits the dual port member and remains coherent until reaching the end of the aerosol storage bag, at which time it diverges and expels all exhaled gas from the aerosol storage bag, thus filling the aerosol storage bag with aerosol. All escaping gas exits the aerosol storage bag via the remaining port of the dual port member, where it escapes into the ambient environment through the ambient port. The remaining dual port of the dual port member, in addition to providing means for escaping gas from the aerosol storage bag, is also in fluid communication with the ambient port and the mouthpiece. Upon inhalation, the patient inhales the aerosol within the aerosol storage bag, the aerosol produced by the nebulizer during inhalation, and ambient air through the ambient port. The cycle is than repeated indefinitely.

An object of the invention is to provide a inhalation therapy device which can store aerosol produced during exhalation for delivery to the patient on the subsequent inhalation.

Another object of the invention is to provide a inhalation therapy device which does not significantly alter the mass median aerodynamic diameter of the aerosol delivered to the patient.

Another object of the invention is to provide a inhalation therapy device which delivers more aerosol to the patient than prior art.

Further objects and advantages of the invention will be brought out in the following portions of the specification, wherein, the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE SPECIFIC EMBODIMENT

Figure 1:
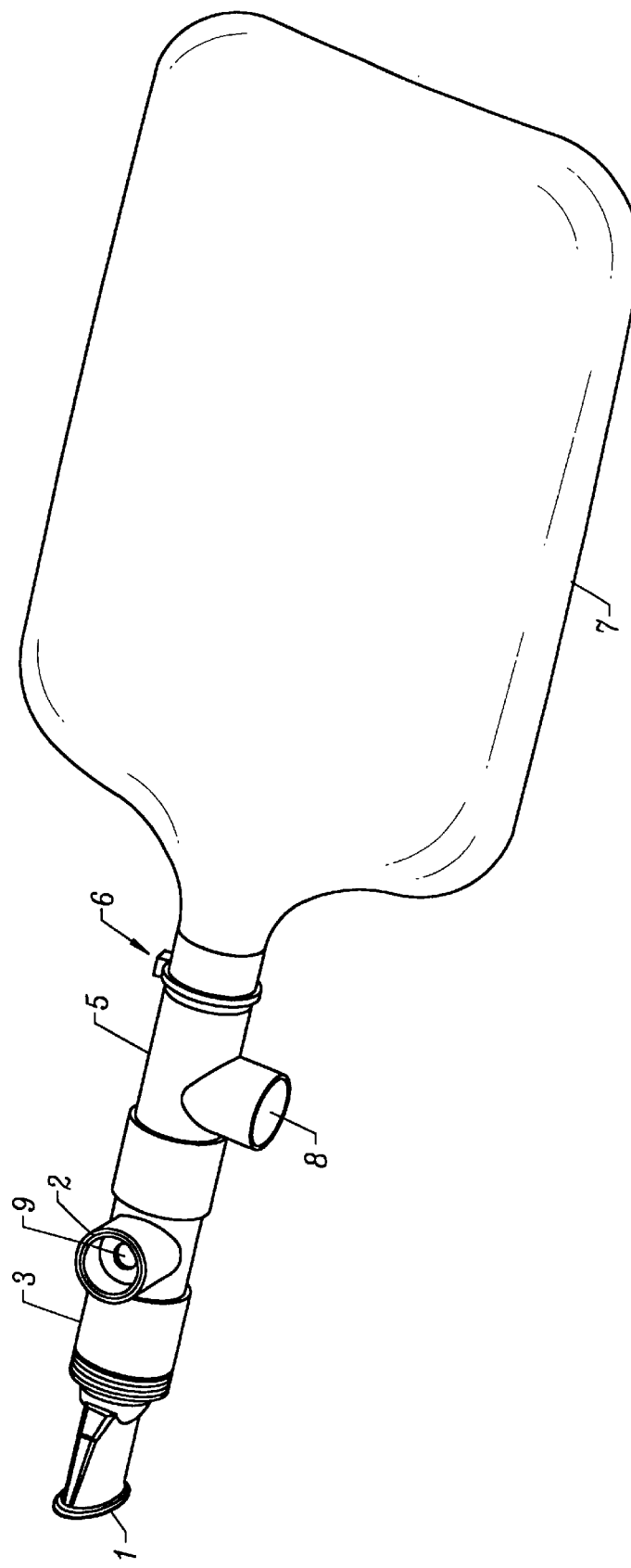
FIG. 1 is a perspective view of the inhalation therapy device.
Figure 2:
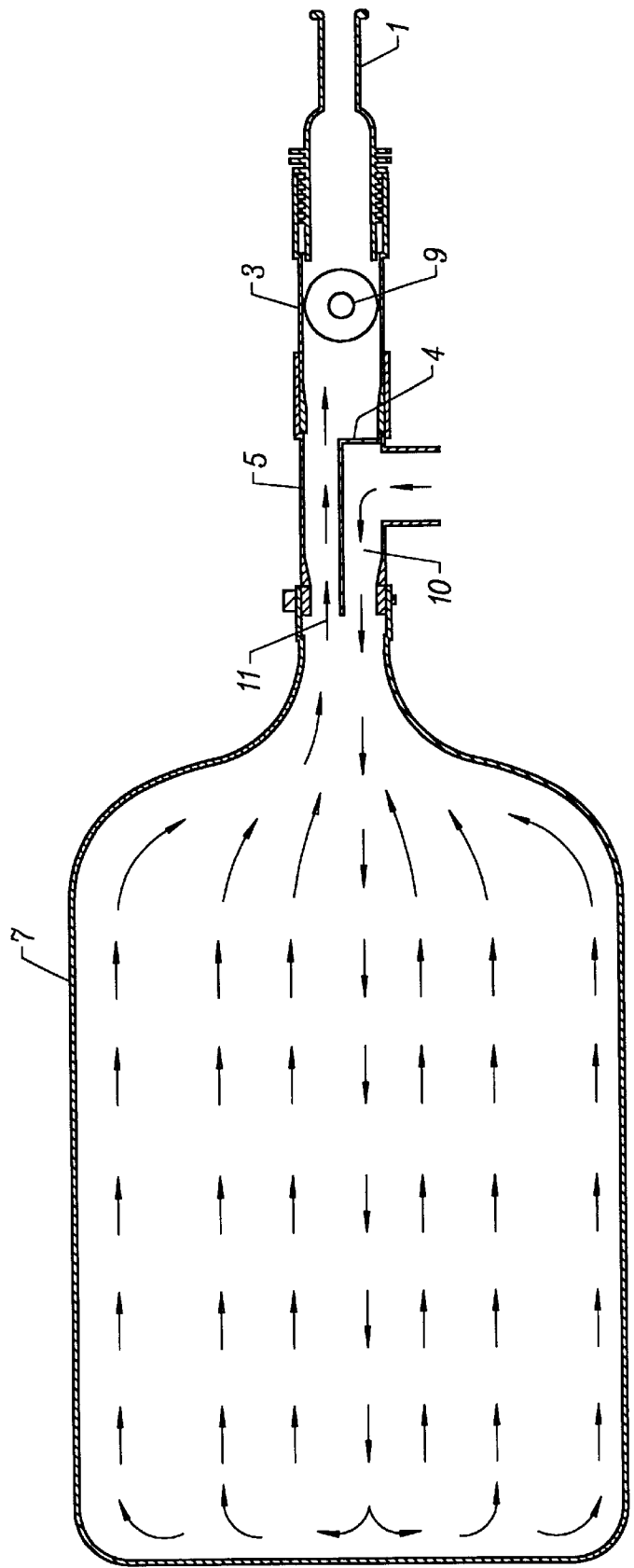
FIG. 2 is a cross-section view of the inhalation therapy device showing the a flow stream within the aerosol storage bag.
Figure 3:
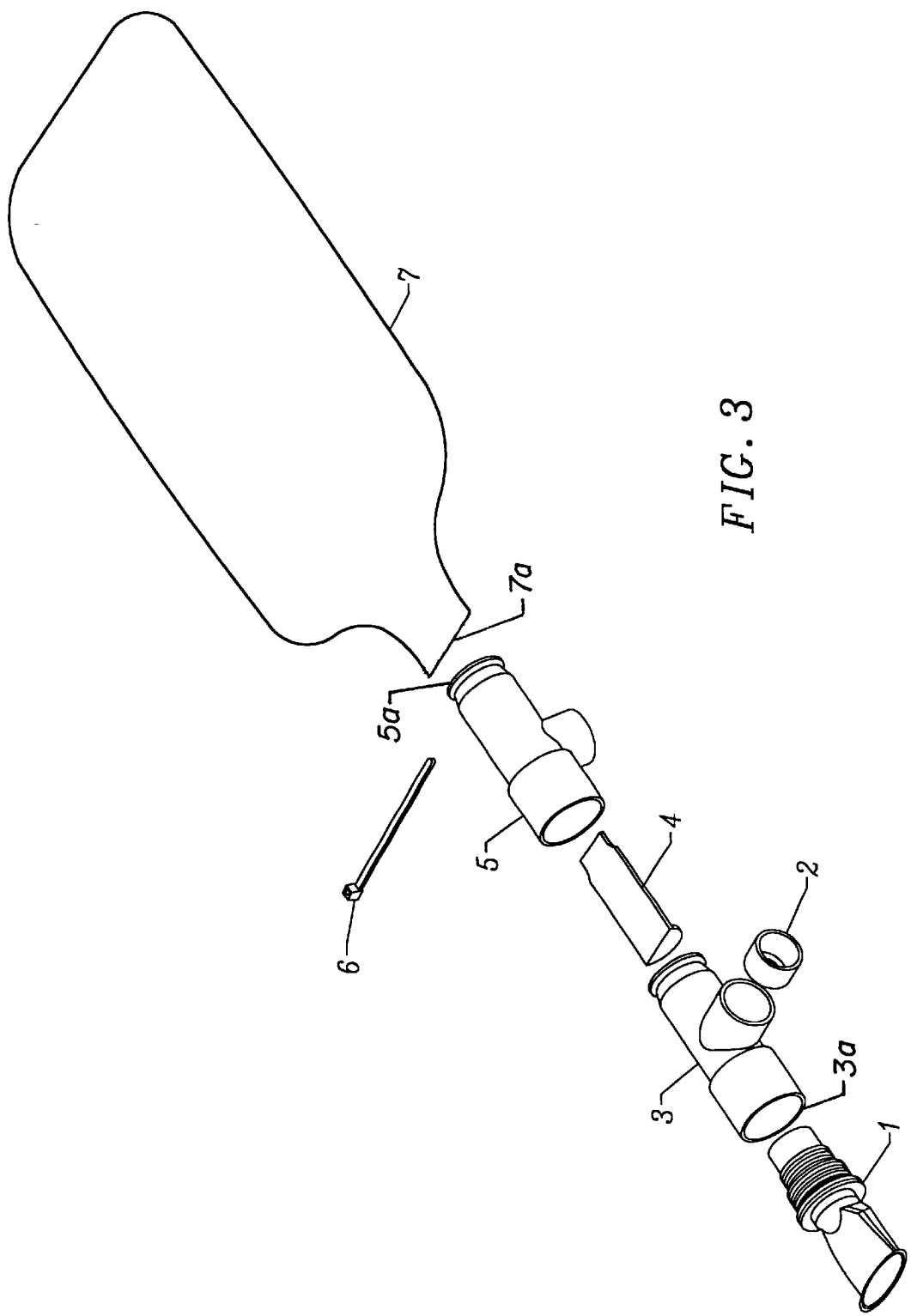
FIG. 3 is a exploded view of the inhalation therapy device.

Referring more specifically to the drawings, for illustrative purposes the present invention is embodied in the apparatus generally shown in FIG. 1 and in detail in FIG. 2 and FIG. 3. It will be appreciated that the apparatus may vary as to configuration and as to details of the parts without departing from the basic concepts as disclosed herein.

Referring to FIG. 1, the present invention includes a nebulizer tee 5 with a nebulizer connection port 8. Nebulizer connection port 8 is a standard ID and taper for connection to most nebulizers. Bilvelel insert 4, which is a generally L-shaped member, inserts into nebulizer tee 5 to form nebulizer port passage 10, also called an aerosol channel 10, and exit passage 11, also called an exit channel 11, parallel to the aerosol channel 10, both channels being in fluid communication with aerosol storage bag 7. Bilevel insert 4 acts as a flow diverter and, with aerosol storage bag 7, is held in place by cable tie 6. Aerosol produced by a nebulizer connected to nebulizer connection port 8 will flow through nebulizer port passage 10 and into aerosol storage bag 7 in the flow pattern as shown in FIG. 2. The aerosol stream exiting nebulizer port passage 10 remains coherent and unmixed with the surrounding gas in aerosol storage bag 7 because the flow profile exiting nebulizer port passage 10 is laminar. Moving gas or fluid is considered laminar or turbulent based on its Reynolds number. If the Reynolds number exceeds 2300 then the flow is considered turbulent, a Reynolds number of less than 2300 indicates laminar flow. The Reynolds number for any conduit carrying fluid may be calculated by the formula $Re=\rho VD/\mu$, where $\rho$ is the density of the fluid, V the average flow velocity; D the equivalent conduit diameter, and $\mu$ the viscosity of the fluid. For circular conduits, the equivalent conduit diameter, D, is simply the inside diameter of the conduit. For non-circular conduits the equivalent diameter may be calculated by the formula $D=4A/P$, where A is the internal cross sectional area of the conduit and P is the inside perimeter of the conduit. Ordinarily, it is taught that fully developed laminar flow would not be generated without a minimum length of fluid travel down a smooth conduit. For this application, this has been shown not to be a requirement for Reynolds numbers less than 1900. In regards to this patent application, the fundamental difference between turbulent and laminar flow is that turbulent flow will become mixed with surrounding gas and laminar flow will not. Laminar flow is essential for the proper working of the present invention. Under turbulent flow conditions incoming aerosol would mix with exhaled gases already in the aerosol storage bag 7 and the patient would be caused to breathe excessive quantities of gas. In the preferred embodiment the Reynolds number for flow passing through the nebulizer port passage 10 simplifies to $Re=4\rho Q/P\mu$ where Q is the volume flow of gas. The perimeter of the preferred embodiment of the present invention is determined as the product of the internal diameter of nebulizer tee 5, which is about 0.7 inch, and the number 2.57. Bilevel insert 4 fits across the entire internal diameter of nebulizer tee 5. Gas exiting aerosol storage bag 7 passes through exit passage 11 and onto the internal volume of ambient tee 3. During assembly ambient tee 3 is inserted into nebulizer tee 5 causing bilevel insert 4 to be fixed into place. During assembly mouthpiece 1 and ambient insert 2 are inserted into ambient tee 3, tees 3 and 5 constituting a main conduit whose two ends are defined as a patient end 3a and a container end 5a, bilevel insert 4 thereby extending from the nebulizer connection port 8 (a first position in the main conduit) to the end 7a of the container. Mouthpiece 1 (a patient connection at the patient end 3a) provides means for a patient to breathe on and receive aerosolized medication from the present invention and may be replaced with a different patient connection such as a mask. Ambient insert 2 is equipped with ambient port 9 at a second position in the main conduit. Ambient port 9 is small enough to provide sufficient resistance to patients breathing to cause the collapsible aerosol storage bag 7 to deflate at least partially on patient's inhalation and inflate at least partially on patient's exhalation. Ambient port 9 may be of an shape and will vary in cross sectional area depending on the targeted patient population. In the current preferred embodiment the ambient port has a cross sectional area of 0.05 square inches.

Assuming air or oxygen as the carrying gas under standard atmospheric conditions, a Reynolds number of less than 2300 can be achieved when (1) the product of the velocity of the aerosol flow along the aerosol channel and the equivalent diameter is no more than 0.032 meter squared per second, (2) the viscosity is about 0.000018 pascal seconds, and (3) the density is about 1.29 kilograms per cubic meter.

An inhalation device in accordance with the present invention can be made by constructing a main conduit, having patient and container ends, with a patient connection at the patient end, an aerosol entry port at a first position, and a flow-resistant ambient port at a second position, and mounting the container end to a collapsible storage container for fluid communication with the interior of the container. Construction of the main conduit can be achieved by forming a laminar-flow aerosol channel fluidly coupling the aerosol entry port with the container interior so that the aerosol flow is at least substantially laminar as it exits the aerosol channel and as it enters the container interior, the aerosol channel having an equivalent diameter. Preferably the present invention is fabricated from a lightweight material such as plastic. It should be noted that nebulizer tee 5, bilevel insert 4, ambient tee 3, and ambient insert 2 may all be injection molded as one piece.

It can be seen, therefore, that the present invention provides a inhalation therapy device which can store aerosol produced by a nebulizer during exhalation and deliver it on the subsequent inhalation. In this way more medication is deliverable to the patient and less is wasted. It should also be noted that the above described nebulizer could also be replaced with any other type of medicinal gas delivery system with the same increase in efficacy. Although the description above contains many specificities, these should not be construed as limiting the scope of the invention but as merely providing illustrations of some of the presently preferred embodiments of this invention.

Any and all patents, patent applications and printed publications referred to above are incorporated by reference.

What is claimed is:

1. An inhalation device comprising:
    a collapsible storage container having a container interior and a container opening;
    a patient connection;
    a main conduit fluidly coupling the container interior to the patient connection;
    an aerosol entry port at a first position along the main conduit;
    a generally L-shaped flow diverter positioned within the main conduit at the first position, the flow diverter dividing a portion of the main conduit into an aerosol channel and an exit channel, the aerosol channel having an at least substantially closed end towards the patient connection and an open end towards the container interior, the aerosol channel shaped so that aerosol flow through the entry port is directed along the aerosol channel in a laminar flow regime into the container interior; and
    a flow-resistant ambient port opening into the main conduit.

2. The inhalation device according to claim 1 wherein the collapsible storage container comprises a bag.

3. The inhalation device according to claim 1 wherein the patient connection comprises a mouthpiece.

4. The inhalation device according to claim 1 wherein the main conduit has a container end secured to the container opening.

5. The inhalation device according to claim 4 wherein in the flow diverter extends from the first position to the container end.

6. The inhalation device according to claim 1 wherein the ambient port opens into the main conduit at a second position between the first position and the patient connection.

7. An inhalation device comprising:
    a collapsible storage bag having a bag interior and a bag opening;
    a mouthpiece;
    a main conduit having a bag end secured to the bag opening and a patient end secured to the mouthpiece so to fluidly couple the storage bag interior to the mouthpiece;
    an aerosol entry port at a first position along the main conduit;
    a flow diverter positioned within the main conduit at the first position to define an aerosol channel having closed end towards the mouthpiece and an open end towards the bag end, so that aerosol flow through the entry port is directed into the container interior;
    the flow diverter dividing a portion of the main conduit into the aerosol channel and an exit channel parallel to the aerosol channel;
    the flow diverter and the main conduit comprising means for creating laminar aerosol flow from the aerosol channel and into the bag; and
    a flow-resistant ambient port opening into the main conduit at a second position between the first position and the patient connection.

8. A method for making an inhalation device comprising:
    constructing a main conduit, having patient and container ends, with an aerosol entry port at a first position, a patient connection at the patient end and a flow-resistant ambient port at a second position;
    mounting the container end to a collapsible storage container, having a container interior, for fluid communication with the container interior and
    the constructing step comprising:
        forming a laminar-flow aerosol channel fluidly coupling the aerosol entry port with the container interior; and
        ensuring flow along the aerosol channel has a Reynolds number of no more than about 2300 so that aerosol flow is at least substantially laminar as it exits the aerosol channel and as it enters the container interior.

9. The method according to claim 8 wherein the ensuring step is carried out so that the Reynolds number is no more than 1900.

* * * * *